United States Patent
Garibyan et al.

(10) Patent No.: US 11,103,387 B2
(45) Date of Patent: Aug. 31, 2021

(54) SYSTEMS AND METHODS FOR REMOVING EXOGENOUS PARTICLES FROM THE SKIN OF A PATIENT

(71) Applicant: THE GENERAL HOSPITAL CORPORATION, Boston, MA (US)

(72) Inventors: Lilit Garibyan, Boston, MA (US); Richard Rox Anderson, Boston, MA (US); William Farinelli, Boston, MA (US); Fernanda H. Sakamoto, Boston, MA (US); Martin Purschke, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 325 days.

(21) Appl. No.: 16/069,339

(22) PCT Filed: Jan. 13, 2017

(86) PCT No.: PCT/US2017/013548
§ 371 (c)(1),
(2) Date: Jul. 11, 2018

(87) PCT Pub. No.: WO2017/124028
PCT Pub. Date: Jul. 20, 2017

(65) Prior Publication Data
US 2018/0311079 A1 Nov. 1, 2018

Related U.S. Application Data

(60) Provisional application No. 62/278,014, filed on Jan. 13, 2016.

(51) Int. Cl.
*A61B 17/20* (2006.01)
*A61M 1/00* (2006.01)
(Continued)

(52) U.S. Cl.
CPC ..... *A61F 13/0203* (2013.01); *A61M 37/0076* (2013.01); *A61B 2017/00769* (2013.01)

(58) Field of Classification Search
CPC .......... A61M 37/0076; A61M 37/0084; A61M 1/0058; A61M 1/0088; A61B 2017/00769; A61F 13/0203
See application file for complete search history.

(56) References Cited

U.S. PATENT DOCUMENTS

2004/0092920 A1* 5/2004 Rozenshpeer ......... A61B 18/02
606/22
2004/0111107 A1 6/2004 Malodobry
(Continued)

FOREIGN PATENT DOCUMENTS

CN 1805714 A 7/2006
WO 2015/021434 A2 2/2015

OTHER PUBLICATIONS

Extended European Search Report for corresponding European Application Serial No. 17739099.4, dated Aug. 26, 2019, pp. 1-10.
(Continued)

*Primary Examiner* — Rebecca E Eisenberg
(74) *Attorney, Agent, or Firm* — Tarolli, Sundheim, Covell & Tummino LLP

(57) ABSTRACT

The present disclosure is directed to systems and methods that removing exogenous particles from a target region of the skin of a patient. The systems and methods can employ dermal lavage to remove the exogenous particles from the target region. In some instances, the exogenous particles can be residual tattoo ink after a tattoo removal process. A conduit can be sized and dimensioned for insertion into or around the target region to inject an irrigation fluid that defines an irrigation area. The exogenous particles can be suspended in the irrigation fluid. A device can be configured
(Continued)

to form one or more channels in the irrigation area so that the exogenous particles are removable from the irrigation area.

10 Claims, 6 Drawing Sheets

(51) Int. Cl.
    *A61F 13/02*         (2006.01)
    *A61M 37/00*      (2006.01)
    *A61B 17/00*        (2006.01)

(56) References Cited

U.S. PATENT DOCUMENTS

| | | |
|---|---|---|
| 2006/0142708 A1 | 6/2006 | Hazut et al. |
| 2007/0156095 A1 | 7/2007 | Hazut et al. |
| 2008/0221548 A1 | 9/2008 | Danenberg et al. |
| 2010/0121259 A1 | 5/2010 | Lutski et al. |
| 2013/0053757 A1 | 2/2013 | O'Neil |
| 2014/0094837 A1 | 4/2014 | Danenberg |
| 2015/0231382 A1 | 8/2015 | Altarac |
| 2018/0119077 A1* | 5/2018 | Ozdoganlar ...... A61M 37/0084 |

OTHER PUBLICATIONS

International Search Report for Application No. PCT/US17/13548 dated Jun. 15, 2017.
Chinese Office Action for corresponding Chinese Application Serial No. 201780017013.1, dated Jun. 18, 2020, pp. 1-10.

* cited by examiner

SYSTEMS AND METHODS FOR REMOVING EXOGENOUS PARTICLES FROM THE SKIN OF A PATIENT

RELATED APPLICATIONS

The present invention is a U.S. National Stage under 35 USC 371 patent application, claiming priority to Serial No. PCT/US2017/013548, filed on 13 Jan. 2017; which claims priority of U.S. Provisional Application No. 62/278,014, filed on 13 Jan. 2016, the entirety of both of which are incorporated herein by reference.

TECHNICAL FIELD

The present disclosure relates generally to systems and methods for removing exogenous particles from a target region of a patient's skin and, more particularly, to systems and methods for tattoo removal.

BACKGROUND

Tattoos are made by inserting ink or other colorant into the dermis of the skin. More than forty million people in the United States have tattoos, and many people will seek to have them removed. While tattoos are considered permanent, it is sometimes possible to fully or partially remove tattoos. Current tattoo removal technologies involve laser treatments (e.g., using Q-switched lasers, picosecond lasers, or the like). To remove the tattoo completely, a patient may be required to undergo a series of painful laser treatments (e.g., requiring 10-20 sessions). Even with multiple sessions, the laser treatments can leave tattoo pigments remaining in the skin and/or create textural changes to the skin, including scarring. Accordingly, many patients are unwilling to have their tattoo removed (even though they no longer want the tattoo) due to the associated time, cost and/or pain.

SUMMARY

The present disclosure relates generally to systems and methods for removing exogenous particles from a target region of a patient's skin and, more particularly, to systems and methods for tattoo removal.

In one aspect, the present disclosure can include a method for removing exogenous particles from a target region of the skin of a patient. The method can include inserting one or more fluid conduits (e.g., perforated fluid conduits, needles, or the like) into a portion of the patient's skin to define an irrigation area in or around the target region. The method can also include injecting an irrigation fluid into the irrigation area so that the exogenous particles become suspended in the irrigation fluid. The method can also include removing the irrigation fluid from the irrigation area. In some instances, the method also can include creating localized edema through endogenous fluid accumulation by injection of histamine, lipases, phospholipases, canthrone, podophylin, or the like.

In another aspect, the present disclosure can include a system for removing exogenous particles from a target region of the skin of a patient. The system can include at least one conduit sized and dimensioned for insertion into or around the target region to define an irrigation area. The at least one conduit can be configured to inject an irrigation fluid into the irrigation area. The system can also include a device configured to form one or more channels in the irrigation area so that the exogenous particles are removable from the irrigation area with the irrigation fluid.

In a further aspect, the present disclosure can include a method for removing a tattoo from a target region of skin of a patient. The method can include shattering the tattoo in the target region into pigment particles. In some instances, the tattoo can be shattered by a laser removal process. In some instances, the method can also include the use of enzymes (e.g., lipases, phospholipases, or the like) to free the tattoo particles from the cells. The method can also include suspending the pigment particles in the irrigation fluid. In other instances, the method can also include adding chemicals to prevent re-phagocytosis of the tattoo particles with the use of sucrose, colchine, podophylin, etc. The method can also include removing the irrigation fluid and the suspended pigment particles from the irrigation area. For example, the irrigation fluid can be removed from the irrigation area via at least one channel through the surface of the skin of the patient.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
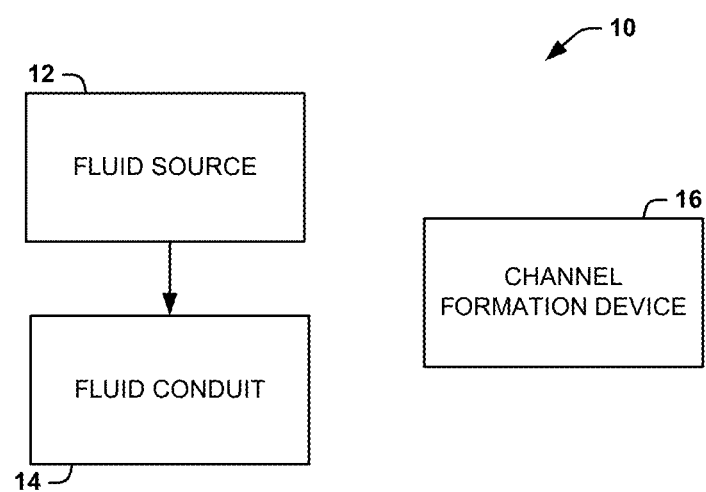
FIG. 1 is a block diagram illustrating an example of a system for removing exogenous particles from a target region of the skin of a patient according to an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "exogenous" can refer to an element or substance that is placed into the body from an external source (e.g., not natural to the body). Accordingly, the term "exogenous particle" can refer to a particle that is placed into the body from an external source. In some instances, an exogenous particle can be an ink pigment that is placed in the skin of a patient. For example, the ink pigment can be a remnant of a tattoo created by a laser removal process.

As used herein, the term "laser removal process" can refer to a process that uses a laser to shatter or fragment ink comprising a tattoo. Examples of laser removal processes can include Q-switched laser removal processes, picosecond laser removal processes, and the like. The terms "laser removal process" and "laser removal therapy" can be used interchangeably herein.

As used herein, the term "skin" can refer to the soft outer covering of vertebrates, including the epidermis (e.g., the outermost layers of cells in the skin) and the dermis (e.g., a layer of skin between the epidermis and subcutaneous tissue that cushions the body from stress and strain).

As used herein, the terms "target region" and "target area" can be used interchangeably and can refer to an area of a patient's skin from which one or more exogenous particles will be removed.

As used herein, the term "irrigation area" can refer to an area of a patient's skin that will be irrigated to remove exogenous particles. In some instances, the irrigation area can be less than, greater than, or equal to the target area.

As used herein, the term "conduit" can refer to an element, structure, or component for conveying a fluid. The conduit can be internal (e.g., needles, microneedles, or the like) and/or external (e.g., a container housing the solution) to a patient's skin. Additionally, when the conduit refers to an external conduit, the conduit can be in contact with the patient's skin (e.g., a component used for electrophoresis, iontophoresis, or the like) or not in contact with the patient's skin.

As used herein, the term "channel" can refer to a passageway or conduit extending from an opening or hole at the surface of the skin to a depth under the skin.

As used herein, the term "microchannel" can refer to a channel with a diameter less than about 1 mm. For example, a microchannel can be a channel that extends from an opening or hole in a patient's skin, through the epidermis, and into the dermis. As an example, a microchannel can be created in a patient's skin by a needle, a laser, or the like.

As used herein, the term "lavage" can refer to washing or irrigating with repeated injections of a fluid (e.g., water, saline, or other biocompatible fluid, which may include a pharmaceutical agent and/or an enzyme and/or any natural products or toxins, such as spider venom, snake venom, beetle venom, bee venom, or the like).

As used herein, the terms "subject" and "patient" can be used interchangeably and refer to any warm-blooded living organism including, but not limited to, a human being, a pig, a rat, a mouse, a dog, a cat, a goat, a sheep, a horse, a monkey, an ape, a rabbit, a cow, etc.

As used herein, the term "operatively coupled" can refer to two or more components that are linked so that they perform their associated function cooperatively and/or in combination.

Overview

The present disclosure relates generally to systems and methods for removing exogenous particles from a target region of a patient's skin and, more particularly, to systems and methods for tattoo removal. After a single laser removal treatment, thousands of microscopic tattoo particles (e.g., exogenous particles) are released from cells in the dermis of the skin. While some of the exogenous particles are washed away by the patient's lymphatic system, other exogenous particles remain in the skin. The remaining exogenous particles, which are engulfed by macrophages and other phagocytes in the skin, essentially preserve the tattoo image. To remove these remaining exogenous particles completely, further laser removal treatments are required. Advantageously, the present disclosure describes systems and methods that can reduce or eliminate the need for further laser removal treatments. In some instances, the systems and methods themselves can eliminate exogenous particles from the patient's skin without the need for an initial laser removal treatment. As discussed in more detailed below, the present disclosure provides systems and methods that employ dermal lavage to remove the remaining exogenous particles from a target region of the patient's skin.

Systems

One aspect of the present disclosure can include a system for removing exogenous particles (e.g., ink particles from a tattoo or residual ink particles in a patient's skin after a tattoo removal process) from a target region of the skin of the patient. The system can utilize dermal lavage to remove the exogenous particles. In some instances, a fluid conduit (e.g., a perforated conduit, one or more microneedles, one or more coring needles, or the like) can be inserted into or around the target region to define an irrigation area. An irrigation fluid can be injected into the irrigation area via the fluid conduit. A device (e.g., a channel formation device) can be configured to form one or more channels in the irrigation area so that the exogenous particles are removable from the irrigation area (e.g., via suction or passive diffusion) along with the irrigation fluid.

FIG. 1 illustrates one example of a system 10 for removing exogenous particles from a target region of the skin of a patient. In some instances, before removing the exogenous particles from the skin, one or more layers of the skin (e.g., the epidermis) can be removed to facilitate removal of the exogenous particles. For example, a suction blister can be created to remove one or more layers of skin. In another example, a fractional laser (e.g., an ablative laser, such as an erbium ablative laser or a $CO_2$ ablative laser) can be used to remove one or more layers of skin. The layers of skin can be removed without scarring (e.g., by use of coring needles or a laser) to improve conventional tattoo removal (e.g., 10% ablation can lead to 10% of the skin/tattoo being removed).

The system 10 can include a fluid source 12, a fluid conduit 14, and a channel formation device 16. Further, as described below, the system 10 can additionally or optionally include one or more pressure devices (not shown) or device(s) (not shown) for imparting a mechanical force on the skin surface. Such pressure devices and/or devices for imparting a mechanical force on the skin surface can be integrated with, operably coupled to, or entirely separate from the fluid source 12, the fluid conduit 14, and/or the channel formation device 16.

As an example, at least a portion of the system 10 can be integrated within a wearable device for removal of the exogenous particles. In the simplest example, the fluid conduit 14 can be one or more hypodermic needles that inject the irrigation fluid from the fluid source 12 into the irrigation area of the patient. The wearable device, which can include the channel formation device 16 (e.g., a laser, one or more needles, one or more microneedles, a coring needle, one or more rolling needles, or the like), can be placed over the irrigation area for a time period to facilitate the removal of the irrigation fluid and the exogenous particles from the irrigation area. In this example, an external negative pressure can be created in a passive manner, such as by movement of the patient's body, which can facilitate the removal of the irrigation fluid and the exogenous particles. The wearable device can also include a reservoir or absorbent material to store the fluid and the exogenous particles removed from the patient's skin. As another example, the wearable device can also include an active pressure source and an accompanying battery. In a further example, the wearable device can include the fluid conduit 14 and the fluid source 12 as a plurality of dissolvable needles (e.g., carbodymethyl cellulose) arranged in an array, each composed of (e.g., filled with) a bolus of irrigation fluid. As the dissolvable needles dissolve, the irrigation fluid can be transported to the irrigation area. In addition to these examples, the wearable device may include additional components. Additionally, it will be noted that the suction can be more effective the longer the alternating pressure, such as positive and negative pressure, suction or pressure is applied (e.g., the suction or pressure being applied for 0, 2, 4, 6, 8, 12, or 24 hours or more would be increasingly more effective).

Figure 2A:
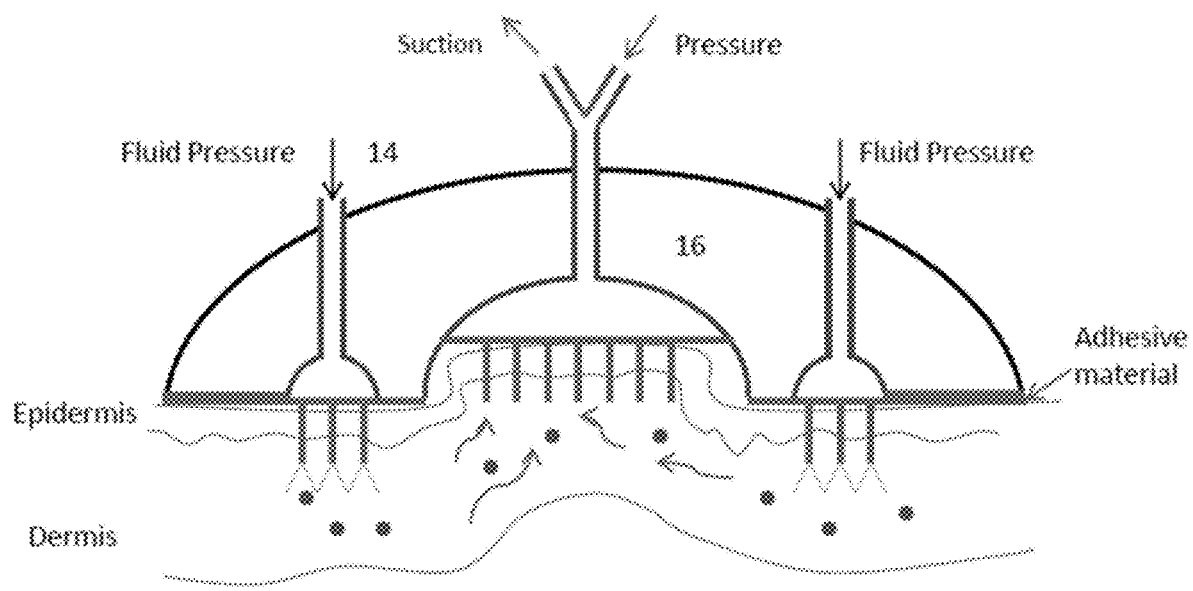
FIG. 2A is a block diagram illustrating an example of a wearable device.
Figure 2B:
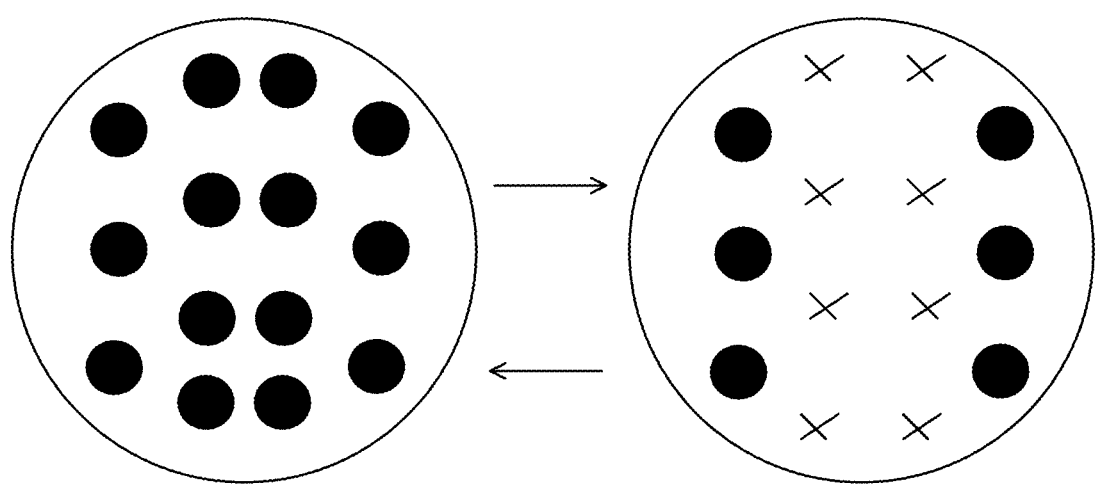
FIG. 2B represents a top view indicating alternating pressure (o) and suction (x) that can be applied by the example wearable device of FIG. 2A.

FIG. 2A shows an example of a wearable device to aid in the lavage of the tattoo ink. The device is held tightly to the skin with an adhesive patch. Small conduits (fluid conduit 14) can enter the skin and pressurized fluid could pass through them. The center chamber (channel formation device 16) allows alternating suction (o) and pressure (x) (shown in FIG. 2B) to flow such that when suction is on, the skin is pulled into the chamber and small conduits pierces the skin and allows suction (o) within the skin to occur, simultaneously causing fluid flow through. After a time, pressure (+) is forced into the chamber and pushes down on to the skin causing movement of the ink particles and flow through the conduits stops. This cycle continues in an alternating pattern. Suction and pressure times could be equal or suction time could be longer then pressure time.

Referring again to FIG. 1, the fluid source 12 can supply an irrigation fluid to the fluid conduit 14, which can be operatively coupled to the fluid source. The irrigation fluid can be a bolus of liquid (e.g., in the range of about 10-50 mL), which is injected through the fluid conduit 14 (e.g., a needle, catheter, or cannula) to the target area to be irrigated. In one example, the fluid source 12 can be a reservoir for the irrigation fluid (e.g., an IV bag). In some instances, the irrigation fluid can be a biocompatible fluid, such as saline, sterile water, or the like. In other instances, the exogenous fluid can include an enzyme, natural compound, and/or a pharmaceutical agent. The enzyme or pharmaceutical agent can at least one of lyse cells, make the skin more porous (e.g., by breaking up the tight connections between collagen fibers in the dermis), prevent or inhibit phagocytosis, or otherwise facilitate removal of the irrigation fluid. Examples of enzymes or pharmaceutical agents that can be within the irrigation fluid include hyuronidase, collegenase, phospholipase, cantherone, colchicine, podophylin, hyaluronic acid, pederine, and sucrose. Examples of a natural compound (e.g., a venom or poison) that can be included in the irrigation fluid include natural or diluted forms of venoms, such as spider, snake, beetle, or bee. In other instances, the enzyme or other chemical agent can be injected before or after the exogenous fluid. For example, the target area can undergo a pre-treatment with histamine, lipase, and/or phospholipase, causing the target area to undergo an inflammatory reaction, which can induce edema and endogenous fluid collection/flow to improve draining of the exogenous particles.

In other instances, the fluid can be an endogenous fluid (e.g., derived or obtained from the patient's body). For example, the endogenous fluid can come from local dermal edema. The patient can be injected with a drug, such as a histamine, that is known to cause local dermal edema in the target region of the skin. The fluid can leave the target region through holes or channels formed by the channel formation device 16, thereby removing the edema and, in the process, washing out the exogenous particles.

In one example, the exogenous particles can include ink particles from a tattoo. In another example, the exogenous particles can be residual tattoo ink particles formed as a result of a tattoo removal process. In either example, the dermal lavage can inject an irrigation fluid into an irrigation area (e.g., an area including at least a portion of the residual tattoo ink) so that the fluid and the residual tattoo ink particles are removed from the skin via one or more holes or channels formed in the target area of the skin by the channel formation device 16.

The fluid conduit 14 can be inserted into a subject's skin in the proximity of the target area. In some instances, the fluid conduit 14 can be inserted around the target area. In other instances, the fluid conduit 14 can be inserted into the target area. The irrigation area can be defined by the injected irrigation fluid, which can be from the fluid source 12.

At least a portion of the exogenous particles in the irrigation area can be suspended in the irrigation fluid as a result. In one example, at least 50% of the exogenous particles in the irrigation area can be suspended in the irrigation fluid. In another example, at least 75% of the exogenous particles in the irrigation area can be suspended in the irrigation fluid. In yet another example, 100% of the exogenous particles in the irrigation area can be suspended in the irrigation fluid.

The channel formation device 16 can be configured to create one or more holes or channels that extend through a portion of the irrigation area. In some instances, the channel formation device 16 can include one or more microneedles. In other instances, the channel formation device 16 can include a laser or an array of a plurality of lasers. In further instances, the channel formation device 16 can be a tattoo gun without any ink ("reverse tattooing"). In one example, the channel formation device 16 is configured to form one or more holes or channels, each of which extends through the epidermis into the dermis. Holes or channels formed by the channel formation device 16 can each have a hydraulic diameter of about 10 mm or less, about 5 mm or less, or about 1 mm or less. In some instances, holes or channels formed by the channel formation device 16 can be microchannels (e.g., having a diameter of at least about 500 Lm). In other instances, an anti-clotting drug, like heparin, aspirin, an NSAID, or other anticoagulant can be used to prevent the closure of the holes or channels formed by the channel formation device 16.

Irrigation fluid, in some instances containing a pharmaceutical agent and/or an enzyme, can be injected into the skin and flow into the one or more holes or channels and then exit the skin with the suspended exogenous particles. In some instances, fluid flow through the holes(s) or channel(s) happens automatically when the hole(s) or channel(s) is/are created in the skin. In other instances, fluid flow occurs upon application of an external stimulus to the target area (e.g., pressure on the surface of the skin by a gloved finger of a medical professional). In still other instances, fluid flow occurs upon application of suction or negative pressure (e.g., from a suction device, such as a breast pump, a wound vacuum, or the like) to the target region. Prior to applying suction, a mechanical force (e.g., a vibration or shock wave) can be applied to the target region to break up attachment of the exogenous particles from the surrounding tissue and make the particles more mobile. As an example, a vibrator can be used as a tool to loosen the exogenous particles. Alternatively, the mechanical force(s) can be applied to the target region following laser therapy (but before formation of the holes or channels) and/or at any point prior to applying suction to the target region.

Suction can be applied continuously or intermittently. Alternatively, suction can be applied in a cyclic manner along with positive pressure to generate a massaging action on the skin and thereby facilitate migration of the exogenous particles to the skin surface. In some instances, the intensity of the suction can be changed over time and thus be applied as a gradient of increasing or decreasing negative pressure.

In some instances, fluid flow can remove about 25% or more of the exogenous particles from the irrigation area, about 50% or more of the exogenous particles from the irrigation area, or about 75% or more of the exogenous particles from the irrigation area.

Methods

Figure 3:
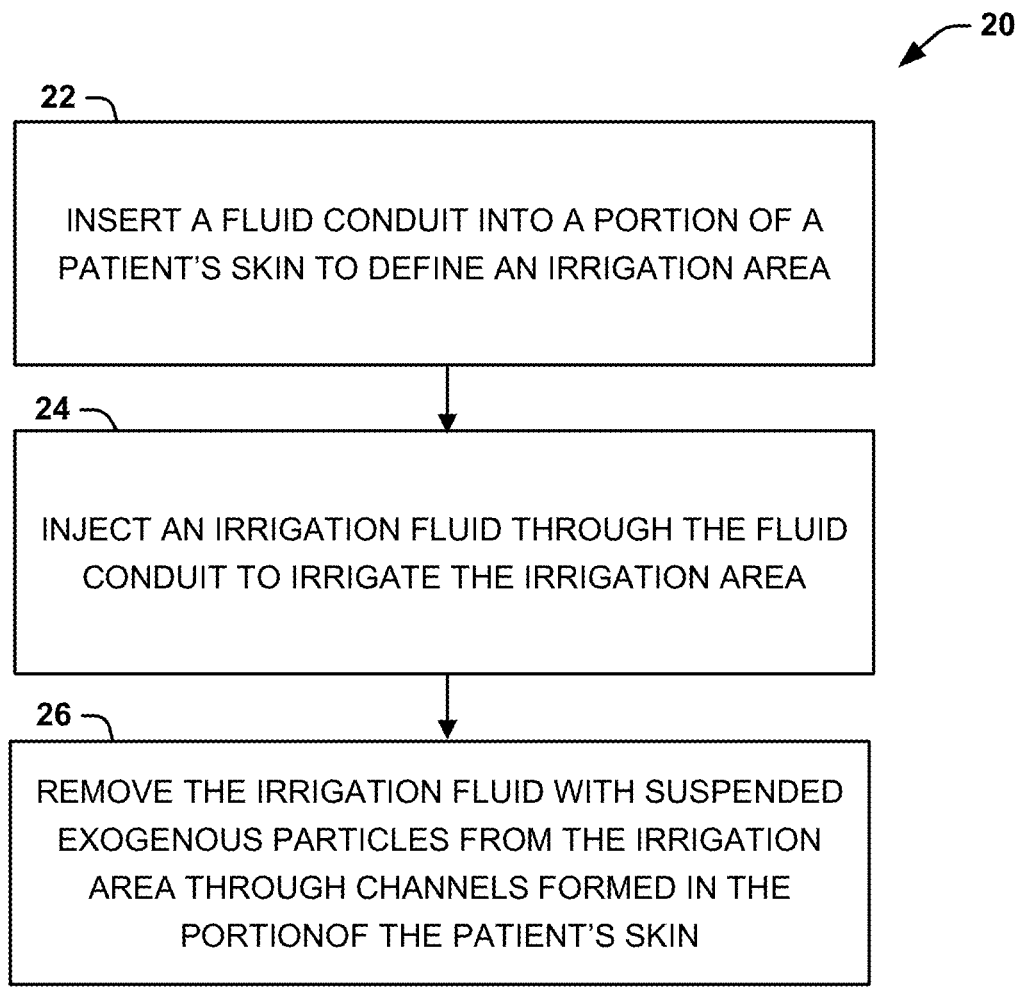
FIG. 3 is a process flow diagram illustrating a method for removing exogenous particles from a target region of skin of a patient according to another aspect of the present disclosure.

Another aspect of the present disclosure can include a method 20 (FIG. 3) for removing exogenous particles (e.g., a tattoo, residual ink particles in a patient's skin, or the like) from a target region of a patient's skin. The method 20 of FIG. 3 is illustrated as a process flow diagram. For purposes of simplicity, the method 20 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 20. The method 20 will be explained with regard to FIGS. 4-6, which illustrate the removal of exogenous particles from a target region of a patient's skin (e.g., using the system 10 described above).

Figure 4:
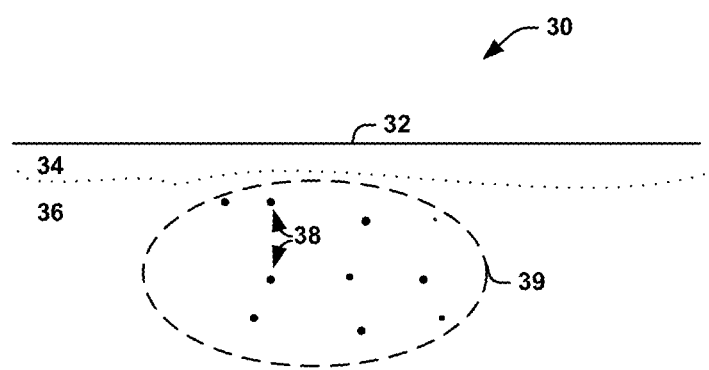
FIGS. 4, 5, and 6A are schematic illustrations showing removal of the exogenous particles from the target region of the skin using the system in FIG. 1.

FIG. 4 is a schematic illustration 30 showing exogenous particles 38 located under the surface of a patient's skin 32. The exogenous particles 38 can include residual tattoo ink particles that remain in the patient's skin after a tattoo removal process (e.g., a Q-switched laser tattoo removal procedure, a picosecond laser tattoo removal procedure, or the like). For example, the exogenous particles 38 can be located in the dermis 36 within a target area 39. In this case, the target area 39 can be defined as an area within the dermis 36 that includes a majority of the exogenous particles 38. For example, the target area 39 can include about 50% or more of the exogenous particles 38, about 75% or more of the exogenous particles, or about 100% of the exogenous particles (e.g., at least about 98% or more). In some instances, before removing the exogenous particles from the skin, one or more layers of the skin (e.g., the epidermis 34) can be removed to facilitate removal of the exogenous particles (as discussed above).

Figure 5:
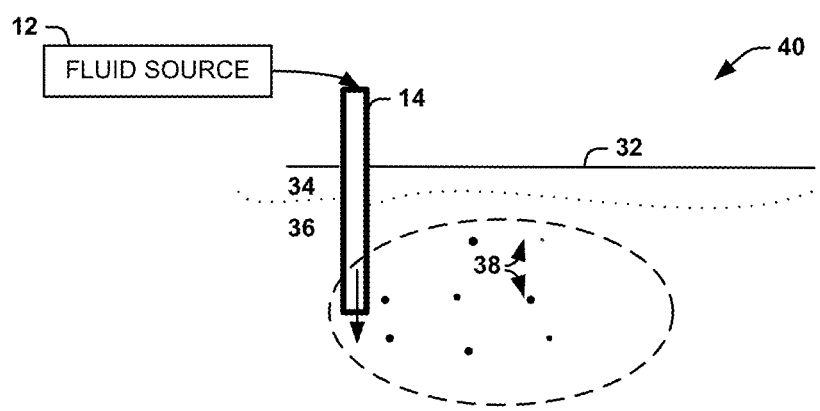

At Step 22, a fluid conduit 14 (FIG. 5) can be inserted into a portion of a patient's skin. The fluid conduit 14 can be operatively coupled to the fluid source 12 and then inserted through the dermis 36 of the patient's skin 32 to define the irrigation area. As shown in FIG. 5, the fluid conduit 14 can be a tube-like structure (e.g., made of a biocompatible polymer) and/or one or more needles (e.g., microneedles, coring needles, or the like), which can inject the irrigation fluid into the target area. Although a single fluid conduit 14 is illustrated, it will be appreciated that a plurality of fluid conduits can be placed to inject the irrigation fluid that defines the irrigation area. It will also be appreciated that multiple fluid sources 12 can be used to deliver fluid to the irrigation area.

Next, at step 24, the irrigation fluid can be injected through the fluid conduit 14 to irrigate the irrigation area. For example, a bolus of the irrigation fluid (e.g., in the range of about 10-50 mL) can be flowed from a fluid source 12, through the fluid conduit 14, and into the target region. In some instances, the exogenous fluid can include an enzyme or a pharmaceutical agent (e.g., hyuronidase, collegenase, phospholipase, cantheradin, cochicine, sucrose, or any other type of enzyme or pharmaceutical agent that can lyse cells, inhibit phagocytosis, keep the exogenous particles free for as long as possible, or the like) or other chemical agent capable of breaking up the tight connections between collagen fibers in the dermis, thereby allowing the irrigation fluid and the exogenous particles to more easily flow out of dermis. In some instances, the enzyme or pharmaceutical agent can be a part of the irrigation fluid. However, in other instances, the enzyme or other chemical agent can be injected before or after the irrigation fluid.

In other instances, the irrigation fluid can be an endogenous fluid. For example, the endogenous fluid can come from local dermal edema. The patient can be injected with a drug, such as a histamine that is known to cause local dermal edema in the target region of the skin. The fluid can leave the target region through holes or channels formed by the channel formation device 16, thereby removing the edema and, in the process, washing out the exogenous particles.

As shown in FIG. 5, the irrigation fluid exits fluid conduit 14 to irrigate the irrigation area (Step 26). As a result, exogenous particles 38 located in the irrigation area are suspended in the irrigation fluid.

Figure 6A:
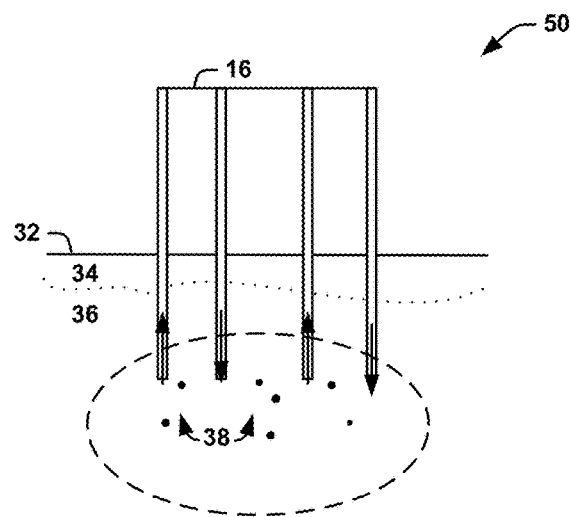
Figure 6B:
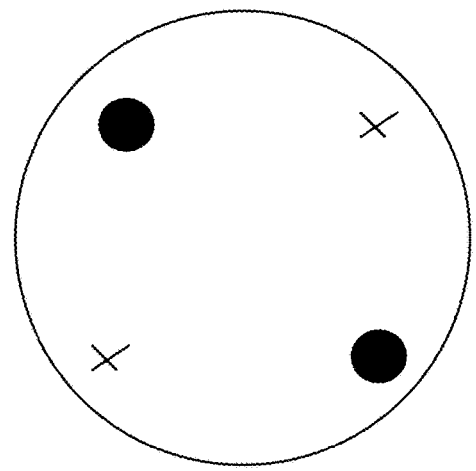
FIG. 6B represents a top view indicating an example of alternating pressure (o) and suction (x) that can be applied by FIG. 6A.

At Step 26, the irrigation fluid is removed from the irrigation area through holes or channels formed in the portion of the patient's skin. As shown in FIG. 6A, a plurality of channels 62-68 (e.g., that enter the dermis 36 through the epidermis 34) can be created within the irrigation area by the channel formation device 16 using, for example, one or more microneedles, one or more coring needles, and/or one or more lasers. In further instances, the channel formation device 16 can be a tattoo gun without any ink. Although four channels 62-68 are illustrated, any number of one or more channels can be created. Additionally, although the channels 62-68 are illustrated as being rectangular, other shapes can be used to perform the same function (e.g., triangular, rounded, square, or the like). Moreover, the channels 62-68 can be separate channels (as illustrated) or at least partially connected or overlapping. The channels 62-68 can be created while the irrigation area is being irrigated. However, it will be appreciated that the channels 62-68 can be created either before the irrigation or after the irrigation. In other instances, an anti-clotting drug, like heparin, aspirin, an NSAID, or other anticoagulant can be used to prevent the closure of the channels formed by the channel formation device 16.

In some instances, the fluid can be removed automatically. In other instances, the fluid requires a catalyst for removal, such as pressure on the patient's skin 32 by a gloved finger of a medical professional or a device that introduces suction. In some instances, about 25% or more of the exogenous particles can be removed along with the fluid. In other instances, about 50% or more of the exogenous particles can be removed along with the fluid. In still other instances, about 75% or more of the exogenous particles can be removed along with the fluid.

In some instances, fluid flow into the channel(s) happens automatically when the channel(s) is/are created in the skin. In other instances, fluid flow occurs upon application of an external stimulus to the target area (e.g., pressure on the surface of the skin by a gloved finger of a medical professional). In still other instances, fluid flow occurs upon application of suction, positive pressure (+), negative pressure (−), or a combination thereof (e.g., from a suction device, such as a breast pump, a wound vacuum, or the like) to the target region. As one example, different pressure patterns can be applied, like −+−, −−−+−−−+−−−+, or the like). As another example, pressure (+) and suction (o) can be applied as shown and described with respect to FIG. 2B. As a further example, shown in FIGS. 6A and 6B, the pressure (+) and suction (o) can be applied together through alternating conduits.

Prior to applying suction, a mechanical force (e.g., a vibration or shock wave) can be applied to the target region to break up attachment of the exogenous particles from the surrounding tissue and make the particles more mobile. Alternatively, the mechanical force(s) can be applied to the target region following laser therapy (but before formation of the channels) and/or at any point prior to applying suction to the target region.

Suction can be applied continuously or intermittently. Alternatively, suction can be applied in a cyclic manner along with positive pressure to generate a massaging action on the skin and thereby facilitate migration of the exogenous particles to the skin surface. In some instances, the intensity of the suction can be changed over time and thus be applied as a gradient of increasing or decreasing negative pressure.

The dermal lavage provided by the method 20 facilitates removal of exogenous particles 38 from the patient's skin 32. For example, the dermal lavage provides a more effective treatment for tattoo removal by reducing the number of laser therapies required to remove the tattoo. This is accomplished by removing the exogenous particles 38 before and/or after they are engulfed by macrophages or other phagocytes in the patient's skin 32. Consequently, any residual tattoo particles remaining after laser therapy are less visible and/or invisible.

From the above description, those skilled in the art will perceive improvements, changes and modifications. Such improvements, changes and modifications are within the skill of one in the art and are intended to be covered by the appended claims.

What is claimed is:

1. A method for removing exogenous particles from a target region of the skin of a patient, comprising:
   inserting one or more fluid conduits into a portion of the patient's skin to define an irrigation area in or around the target region;
   injecting an irrigation fluid through the one or more fluid conduits to irrigate the irrigation area, wherein the exogenous particles become suspended in the irrigation fluid; and
   removing the irrigation fluid from the irrigation area via one or more channels, wherein pressure is applied continuously or intermittently as a negative pressure for a first period of time and a positive pressure for a different second period of time to the irrigation area to facilitate removal of the irrigation fluid and at least a portion of the exogenous particles therefrom.

2. The method of claim 1, wherein the irrigation fluid comprises an enzyme, a natural venom, or a pharmaceutical agent, wherein the enzyme or the pharmaceutical agent is capable of at least one of lysing cells, making the skin more porous, preventing or inhibiting phagocytosis, creating localized edema, and facilitating removal of the irrigation fluid.

3. The method of claim 1, wherein the exogenous particles comprise shattered tattoo pigments formed as a result of a Q-switched or a picosecond laser therapy to the target region.

4. The method of claim 3, wherein a mechanical force is applied to the target region after application of the laser therapy.

5. The method of claim 1, wherein at least a portion of the epidermis comprising the target area is removed prior to the circulating step.

6. The method of claim 1, wherein an anticoagulant is added to the irrigation fluid to ensure that the one or more channels remain open.

7. A system for removing exogenous particles from a target region of the skin of a patient, comprising:
   at least one conduit sized and dimensioned for insertion into or around the target region to define an irrigation area, the at least one conduit being configured to inject an irrigation fluid into the irrigation area;
   a device configured to form one or more channels in the irrigation area so that the exogenous particles are removable from the irrigation area with the irrigation fluid; and
   a pressure source configured to apply pressure continuously or intermittently as a negative pressure for a first period of time and a positive pressure for a different second period of time to the irrigation area to facilitate removal of the irrigation fluid and at least a portion of the exogenous particles therefrom.

8. The system of claim 7, wherein the conduit is dissolvable and comprises the irrigation fluid.

9. The system of claim 7, wherein the irrigation fluid comprises:
   at least one of saline and water; and
   at least one of an enzyme, a natural venom, and a pharmaceutical agent that is capable of at least one of lysing cells, making the skin more porous, preventing or inhibiting phagocytosis, creating localized edema and facilitating removal of the irrigation fluid.

10. The system of claim 7, wherein the exogenous particles comprise shattered tattoo pigments formed as a result of a Q-switched or a picosecond laser therapy to the target region.

* * * * *